(12) United States Patent
Seo et al.

(10) Patent No.: US 11,756,193 B2
(45) Date of Patent: Sep. 12, 2023

(54) METHOD AND APPARATUS FOR DIAGNOSING ALZHEIMER'S DISEASE USING PET-CT IMAGE

(71) Applicant: SAMSUNG LIFE PUBLIC WELFARE FOUNDATION, Seoul (KR)

(72) Inventors: Sang Won Seo, Seoul (KR); Soo Jong Kim, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 0 days.

(21) Appl. No.: 17/251,959

(22) PCT Filed: Dec. 1, 2020

(86) PCT No.: PCT/KR2020/017362
§ 371 (c)(1),
(2) Date: Jan. 29, 2021

(87) PCT Pub. No.: WO2022/030692
PCT Pub. Date: Feb. 10, 2022

(65) Prior Publication Data
US 2023/0153991 A1     May 18, 2023

(30) Foreign Application Priority Data
Aug. 3, 2020   (KR) .................. 10-2020-0096623

(51) Int. Cl.
*A61B 6/00*     (2006.01)
*G06T 7/00*     (2017.01)
(Continued)

(52) U.S. Cl.
CPC ............ *G06T 7/0012* (2013.01); *A61B 6/032* (2013.01); *A61B 6/037* (2013.01); *A61B 6/501* (2013.01);
(Continued)

(58) Field of Classification Search
CPC ......... G06T 7/0012; G06T 2207/10081; G06T 2207/10104; G06T 2207/30016;
(Continued)

(56) References Cited

U.S. PATENT DOCUMENTS

| | | | |
|---|---|---|---|
| 2013/0203245 A1 | 8/2013 | Campbell | |
| 2016/0239968 A1* | 8/2016 | Parsey | ................ A61B 5/0042 |
| 2019/0298291 A1* | 10/2019 | Yang | ..................... A61B 6/032 |

FOREIGN PATENT DOCUMENTS

| | | |
|---|---|---|
| KR | 101757646 B1 | 7/2017 |
| KR | 102004964 B1 | 7/2019 |

OTHER PUBLICATIONS

Cho et al. "A new Centiloid method for 18F-florbetaben and 18F-flutemetamol PET without conversion to PiB" European Journal of Nuclear Medicine and Molecular Imaging (2020) 47:1938-1948.

(Continued)

*Primary Examiner* — Siamak Harandi
(74) *Attorney, Agent, or Firm* — Myers Bigel, P.A.

(57) ABSTRACT

A method of diagnosing Alzheimer's disease using a positron emission tomography-computed tomography (PET-CT) image may include generating a standard brain CT template in a Montreal Neurological Institute (MNI) region based on a CT image calculated from a PET-CT apparatus, calculating a whole cortex volume of interest (VOI) for a plurality of detail regions capable of being used in $^{18}$F-florbetaben (FBB) and $^{18}$F-flutemetamol (FMM) in common within a cortex ROI region in which a deposition of beta amyloid (Continued)

protein is equal to or higher than a given value based on the standard brain CT template, and calculating a centiloid of each of the plurality of detail regions based on an amyloid standardized uptake value ratio (SUVR) of each of the plurality of detail regions.

8 Claims, 5 Drawing Sheets

(51) Int. Cl.
      *G06V 10/25*     (2022.01)
      *A61B 6/03*     (2006.01)

(52) U.S. Cl.
      CPC ............ *A61B 6/5217* (2013.01); *G06V 10/25* (2022.01); *G06T 2207/10081* (2013.01); *G06T 2207/10104* (2013.01); *G06T 2207/30016* (2013.01)

(58) Field of Classification Search
      CPC ........... G06T 7/00; A61B 6/032; A61B 6/037; A61B 6/501; A61B 6/5217; A61B 5/4088; A61B 8/4416; A61B 8/5223; A61B 8/5261; G06V 10/25
      See application file for complete search history.

(56) References Cited

OTHER PUBLICATIONS

Tuszynski et al. "Evaluation of software tools for automated identification of neuroanatomical structures in quantitative β-amyloid PET imaging to diagnose Alzheimer's disease" European Journal of Nuclear Medicine and Molecular Imaging (2016) 43:1077-1087.

* cited by examiner

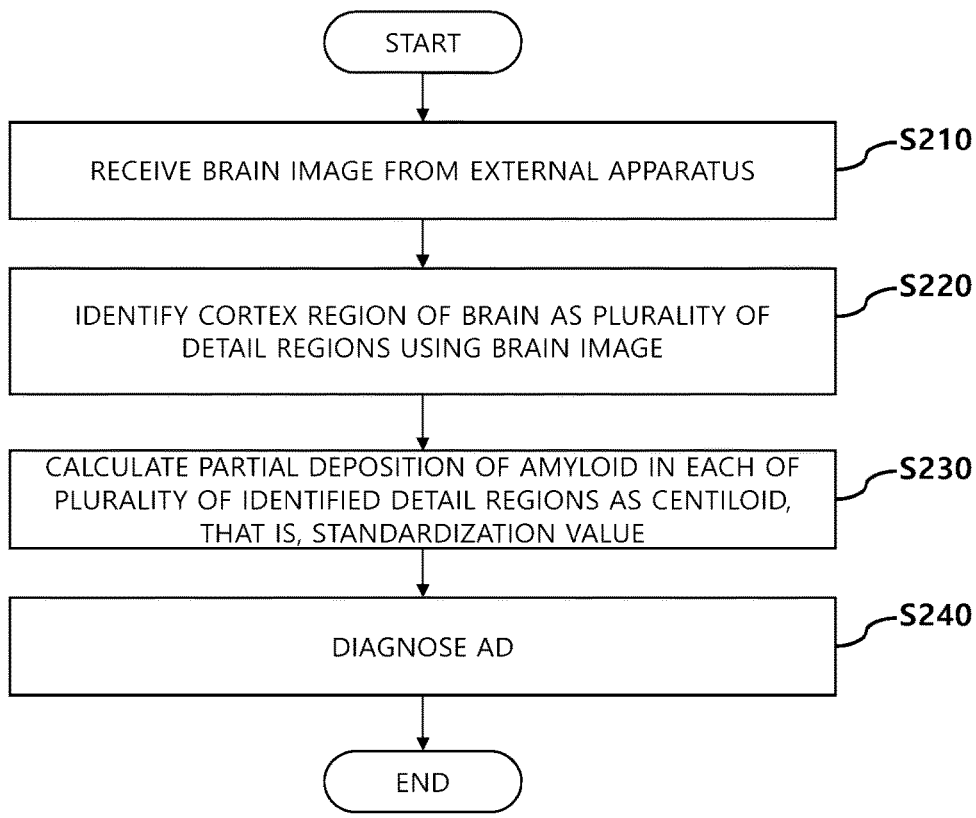
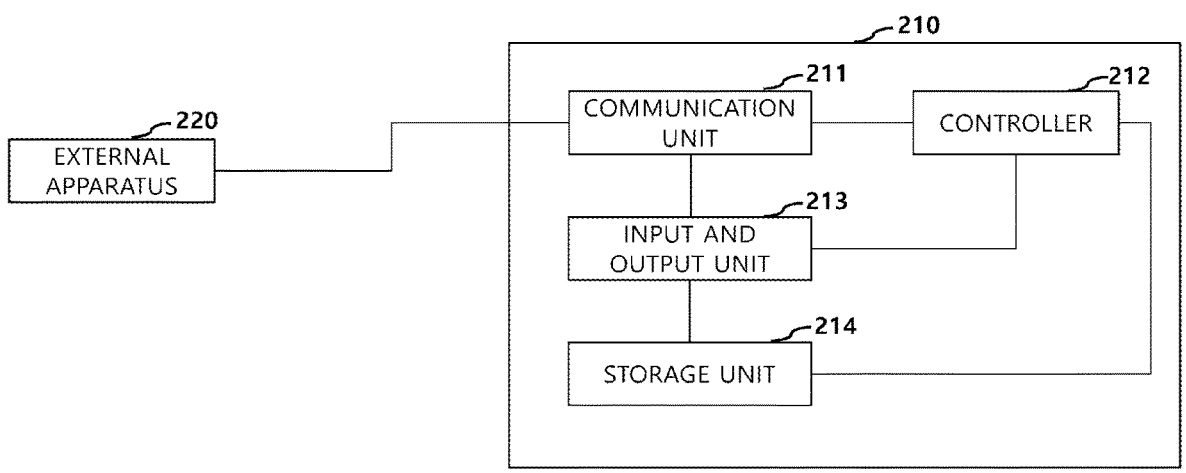

METHOD AND APPARATUS FOR DIAGNOSING ALZHEIMER'S DISEASE USING PET-CT IMAGE

BACKGROUND

1. Technical Field

The present disclosure relates to a method and apparatus for diagnosing Alzheimer's disease (AD) based on a centiloid, and more particularly, to a method and apparatus for diagnosing AD using a PET-CT image, that is, an output of a PET-CT scanner.

2. Related Art

Recently, persons who have a cognitive impairment attributable to Alzheimer's disease (AD) are increasing along with the progress of aging. Most of medicines for AD developed so far are cholinesterase inhibitors (ChEI) and also include an N-methyl-D-aspartate (NMDA) receptor antagonist. However, these medicines have their limitations in that the efficacy thereof is exhibited in the initial step of the disease.

Proteins known as a cause of AD include tau proteins and beta amyloid proteins (amyloid-$\beta$, A$\beta$) (also called "amyloid beta" or "amyloid"). A degree of the progress of AD may be determined and the degradation in the cognitive function may be predicted, based on whether these cause proteins are accumulated in the brain. These cause proteins may function as bio markers for AD.

In order to slow down the progression speed of AD, it is necessary to initially diagnose a mild cognitive impairment (MCI) and AD. The importance of determining these cause proteins as bio markers is increasing.

In order to determine beta amyloid of the cause proteins, a neuropsychological factor, a genetic factor, and an aged statistical factor for evaluating the cognitive function, and result information using various tools, such as brain imaging-based tools including magnetic resonance imaging (MRI), computed tomography (CT), positron emission tomography (PET), single photon emission computed tomography (SPECT), and PET-CT, may be used as variables for analysis. A tool for determining beta amyloid is gradually diversified.

In relation to the determination of beta amyloid, Korean Patent Application Publication No. 10-2019-0067477 (entitled "A MEASURING METHOD AND APPARATUS OF ALZHEIMER'S DISEASE CLINICAL STAGE USING AMYLOID PET") discloses a process of obtaining data related to a standardized uptake value ratio (SUVR) of amyloid in the brain, analyzing the amyloid SUVR, classifying patients as any one of a plurality of preset groups based on an amyloid SUVR in the underlying structure of a brain cortex, and estimating a clinical stage. However, the process does not consider a different degree of an amyloid uptake in a brain portion for each patient and has a limit such as a change in quantitative values due to a difference in an analysis method for amyloid PET or a difference in a radiopharmaceutical for diagnosis.

Accordingly, in order to determine a degree of the uptake of amyloid, a centiloid, that is, standardized information capable of reducing a change in quantitative values, needs to be considered. In order to consider the centiloid score, there is a need for a method for considering a degree of the uptake of amyloid depending on a detail region of the brain.

PRIOR ART DOCUMENT

Patent Document (Patent Document) Korean Patent Application Publication No. 10-2019-0067477 (Jun. 17, 2019)

SUMMARY

Various embodiments are directed to providing a method and apparatus for diagnosing Alzheimer's disease (AD) using a PET-CT image, which can calculate a centiloid in each detail region of the brain based on only an image using a PET-CT apparatus without performing an MRI scan and diagnose AD using the calculated centiloid for each detail region.

In an embodiment, a method of diagnosing Alzheimer's disease using a positron emission tomography-computed tomography (PET-CT) image may include generating a standard brain CT template in a Montreal Neurological Institute (MNI) region based on a CT image calculated from a PET-CT apparatus, calculating a whole cortex volume of interest (VOI) for a plurality of detail regions capable of being used in $^{18}$F-florbetaben (FBB) and $^{18}$F-flutemetamol (FMM) in common within a cortex ROI region in which a deposition of beta amyloid protein is equal to or higher than a given value based on the standard brain CT template, and calculating a centiloid of each of the plurality of detail regions based on a whole cortex VOI and amyloid standardized uptake value ratio (SUVR) of each of the plurality of detail regions.

In some embodiments, the plurality of detail regions may include at least two of a frontal cortex, a temporal cortex, a parietal cortex, an occipital cortex, a posterior cingulate cortex, a striatum cortex, and an insula and cingulum cortex.

In some embodiments, the PET-CT image may be calculated using any one of $^{18}$F-florbetaben (FBB) and $^{18}$F-flutemetamol (FMM) as a radio-pharmaceutical tracer.

In some embodiments, the centiloid may be calculated as a value obtained by subtracting a second previously calculated value from a result value of a real number times a first previously calculated value with respect to the amyloid SUVR.

In some embodiments, the PET-CT image may include a PET image and a CT image as a result of a beta amyloid PET apparatus.

In another embodiment, an apparatus for diagnosing Alzheimer's disease using a PET-CT image may include a template generation unit configured to generate a standard brain CT template in a Montreal Neurological Institute (MNI) region based on a CT image calculated from a PET-CT apparatus, a detail region identification unit configured to calculate a whole cortex volume of interest (VOI) for a plurality of detail regions capable of being used in $^{18}$F-florbetaben (FBB) and $^{18}$F-flutemetamol (FMM) in common within a cortex ROI region in which a deposition of beta amyloid protein is equal to or higher than a given value based on the standard brain CT template, and a centiloid calculation unit configured to calculate a centiloid of each of the plurality of detail regions based on the whole cortex VOI and an amyloid standardized uptake value ratio (SUVR) of each of the plurality of detail regions.

In some embodiments, the plurality of detail regions may include at least two of a frontal cortex, a temporal cortex, a parietal cortex, an occipital cortex, a posterior cingulate cortex, a striatum cortex, and an insula and cingulum cortex.

In some embodiments, the PET-CT image may be calculated using any one of $^{18}$F-florbetaben (FBB) and $^{18}$F-flutemetamol (FMM) as a radio-pharmaceutical tracer.

In some embodiments, the centiloid may be calculated as a value obtained by subtracting a second previously calculated value from a result value of a real number times a first previously calculated value with respect to the amyloid SUVR.

In some embodiments, the PET-CT image may include a PET image and a CT image as a result of a beta amyloid PET apparatus.

BRIEF DESCRIPTION OF THE DRAWINGS

FIG. 1 is a flowchart for describing a method of diagnosing Alzheimer's disease (AD) using a PET-CT image according to an embodiment of the present disclosure.

FIG. 2 illustrates a structure for describing an apparatus for diagnosing AD using a PET-CT image according to an embodiment of the present disclosure.

DETAILED DESCRIPTION

Figure 3:
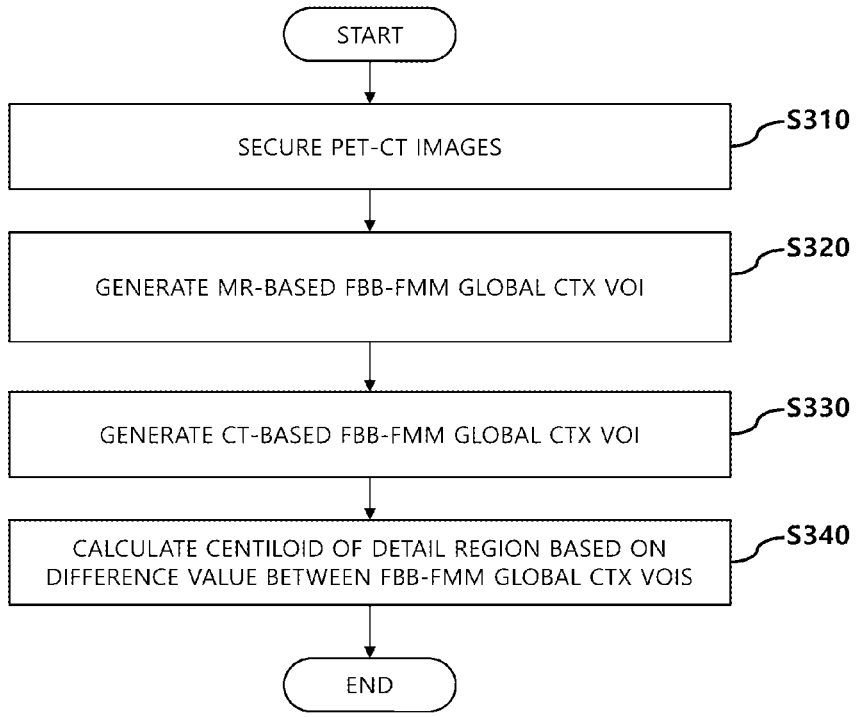
FIG. 3 is a flowchart for verifying the method and apparatus for diagnosing AD using a PET-CT image according to an embodiment of the present disclosure.

Hereinafter, terms used in this specification are briefly described, and configurations and actions according to embodiments of the present disclosure are described in detail as detailed contents for carrying out the present disclosure.

Terms used in the present disclosure are common terms currently and widely used by taking into consideration functions in the present disclosure, but the terms may be changed depending on an intention of a technician skilled in the art, a precedent, or the advent of a new technology. Furthermore, in a specific case, some terms are randomly selected by the applicant. In this case, the meaning of a corresponding term will be described in detail in the corresponding description of the invention. Accordingly, terms used in the present disclosure should be defined based on their substantial meanings and contents over the present disclosure, not the simple names of the terms.

In the entire specification, unless explicitly described to the contrary, the word "include" will be understood to imply the further inclusion of stated elements, not the exclusion of any other elements. Furthermore, the term " . . . unit" or "module" described in the specification means a unit for processing at least one function or operation, and the unit may be implemented by hardware or software or a combination of hardware and software. Furthermore, throughout the specification, when it is described that one part is "connected" to another part, the one part may be "directly connected" to the another part or may be "indirectly connected" to the another part "with a still another part interposed therebetween."

Embodiments of the present disclosure are described hereinafter in detail with reference to the accompanying drawings, in order for a person having ordinary skill in the art to which the present disclosure pertains to easily carry out the present disclosure. The present disclosure may be implemented in various different ways, and is not limited to the disclosed embodiments herein. In the drawings, in order to clearly describe the present disclosure, a description of parts unrelated to the description is omitted, and similar reference numbers are used to refer to similar parts throughout the specification.

Proteins known as a cause of Alzheimer's disease (AD) include tau proteins and beta amyloid. A degree of the progress of AD may be determined based on whether these cause proteins are accumulated in the brain. Thus, these cause proteins may function as bio markers for AD. In order to determine beta amyloid, that is, in order to measure whether beta amyloid is accumulated in the brain, brain imaging apparatuses, such as a magnetic resonance imaging (MRI) apparatus, a computed tomography (CT) apparatus, a positron emission tomography (PET) apparatus, and a PET-CT apparatus (or scanner), may be used.

A result or output of the MRI apparatus may be denoted as an MRI image. A result or output of the CT apparatus may be denoted as a CT image. A result or output of the PET apparatus may be denoted as a PET image. A result or output of the PET-CT apparatus may be denoted as the PET-CT image.

The PET-CT apparatus is an apparatus in which the PET apparatus and the CT apparatus are combined. The PET-CT apparatus may generate an anatomical image (i.e., CT image) and functional image (i.e., PET image) of a disease as one image, and may generate and output a CT image and a PET image by separating the CT image and the PET image. The PET-CT apparatus may also be denoted as a fusion-CT apparatus. The CT apparatus used in the PET-CT apparatus may be a low dose CT apparatus, and images and contents thereof may be different from a common CT image. A common CT apparatus finds out a structural change in the human body, whereas the PET-CT apparatus can determine a state in a biochemical change step, that is, a previous step in which a structural change occurs. Accordingly, the PET-CT apparatus may be suitable for a diagnosis of AD according to the deposition of beta amyloid.

In general, in order to measure the deposition of beta amyloid in vivo, a PET apparatus is used. The PET apparatus is used as a bio marker important for a diagnosis of AD. Among the PET apparatuses, an amyloid PET (PET) apparatus may be used. The amyloid PET apparatus may be used to measure the presence or amount of beta amyloid deposited in the brain. The amyloid PET apparatus may check the presence of amyloid deposited in the brain, by combining a material, well combined with amyloid, and radioactive isotopes (carbon radioactive isotopes ($C^{11}$) or fluorine isotopes ($F^{18}$)) and injecting the combination into a patient.

Conventionally, in order to diagnose AD, the related art requires a process of obtaining a PET-CT image from the PET-CT apparatus and verifying a correlation between the PET apparatus and the CT apparatus based on a comparison between a standard brain CT template generated in a Montreal Neurological Institute (MNI) region and an MNI template generated based on an MRI image. Specifically, conventionally, a centiloid may be used for a diagnosis of AD. In order to obtain a more accurate centiloid, a brain MRI image of a patient is necessary in addition to a PET-CT image. A patient with AD has to take two tests through the MRI apparatus and the PET apparatus.

In this case, it is difficult to use the MRI apparatus for a patient, who has claustrophobia, due to a long photographing time. The MRI apparatus has disadvantages in that a metal material, such as a metallic prosthetic tooth or spine prosthesis, becomes a hindrance to a diagnosis using the MRI apparatus even though the amount of the metal material is very small and the MRI apparatus may hinder an operation of an artificial inner ear or a permanent type pacemaker. As a result, there is a need for a method of diagnosing AD based on only an anatomical PET-CT image obtained by the PET-CT apparatus or measuring a centiloid used to diagnose AD because MRI images of all patients cannot be obtained by applying the MRI apparatus to the patient.

A method and apparatus for diagnosing AD using a PET-CT image according to an embodiment of the present disclosure can divide the cortex of the brain into detail regions based on only one imaging result using the PET-CT apparatus without using the MRI apparatus, can calculate a centiloid for each of the detail regions, and can diagnose AD. Accordingly, expenses can be reduced, and AD can be diagnosed with respect to a patient whose imaging using the MRI apparatus is difficult, by using a bio marker called a centiloid.

Hereinafter, detailed embodiments of the present disclosure are described with reference to the accompanying drawings.

FIG. 1 is a flowchart for describing a method of diagnosing Alzheimer's disease (AD) using a PET-CT image according to an embodiment of the present disclosure. FIG. 2 illustrates a structure for describing an apparatus 210 for diagnosing AD using a PET-CT image according to an embodiment of the present disclosure.

The following descriptions will be made with reference to FIGS. 1 and 2 together because the method of diagnosing AD in FIG. 1 is performed by the apparatus for diagnosing AD in FIG. 2.

Referring to FIG. 1, a communication unit 211 of the apparatus 210 for diagnosing AD using a PET-CT image may receive a brain image from an external apparatus 220 (S210). In some embodiments, the external apparatus 220 may be a brain imaging apparatus, and may be any one of a magnetic resonance imaging (MRI) apparatus, a computed tomography (CT) apparatus, a positron emission tomography (PET) apparatus, and a PET-CT apparatus (or scanner), for example. Preferably, the external apparatus may be a PET-CT apparatus (or amyloid PET-CT apparatus or amyloid PET).

In some embodiments, the brain image may be a PET-CT image. The external apparatus 220 and the apparatus 210 for diagnosing AD using a PET-CT image may directly transmit or receive a brain image through wired or wireless communication. The external apparatus 220 and the apparatus 210 for diagnosing AD using a PET-CT image may indirectly transmit or receive a brain image through systems within hospitals connected thereto, respectively.

The communication unit 211 may transmit, to a controller 212, the brain image received from the external apparatus 220. The controller 212 may identify a cortex region of the brain as a plurality of detail regions based on the brain image (S220), and may calculate a partial deposition of amyloid in each of the plurality of identified cortex detail regions as a centiloid, that is, a standardization value (S230).

Quantitative values of amyloid PET are different due to a difference in the analysis method or a difference in a radiopharmaceutical for tracking, and thus a method of standardizing the quantitative values is necessary. Accordingly, the controller 212 may calculate a centiloid (CL) as a standardization score calculated based on amyloid by using an average of amyloid negative targets as 0 and an average of patients having typical AD as 100. In other words, the centiloid may indicate a unit scored using an average value of sure amyloid negative targets as 0 and an average value of typical AD patients as 100, regardless of results obtained from amyloid PET.

In some embodiments, the controller 212 may generate or identify an amyloid PET-CT image of each of two radio-pharmaceutical tracers based on the received brain image, and may calculate a centiloid for each of the plurality of detail regions, which may be applied to an amyloid PET-CT image of each of the two radio-pharmaceutical tracers in common. In some embodiments, the radio-pharmaceutical tracer is an amyloid PET tracer. For example, the two radio-pharmaceutical tracers may be $^{18}$F-florbetaben (FBB) and $^{18}$F-flutemetamol (FMM).

In some embodiments, the controller 212 may calculate quantitative values of the centiloid in a cortex region of the brain in which amyloid beta is mainly deposited in the amyloid PET-CT image.

In some embodiments, the controller 212 may calculate a centiloid for each of a plurality of detail regions for a diagnosis of AD by subdividing a brain portion of an AD patient into the plurality of detail regions because the amount of amyloid beta deposited in the brain portion is different for each patient, may divide a region within a cortex region of the brain, and may calculate amyloid beta, deposited in a partial region, as a the centiloid, that is, a standardization value, in an amyloid PET-CT image of the patient based on the centiloid for each of the plurality of detail regions.

In some embodiments, the controller 212 may use a whole cerebellum as a reference region, may calculate a standardized uptake value ratio (SUVR) and centiloid of each of the plurality of detail regions, and may use an equation for calculating the SUVR and centiloid, which is received from a storage unit 214. The amount of deposited amyloid in the amyloid PET-CT image may be calculated by relatively quantifying the amount of amyloid in a region to be analyzed based on a region having no amyloid. In this case, a region of the brain having no amyloid is called a reference region. The amount of amyloid can be accurately quantified only if a proper reference region is set. In general, a region to be analyzed in an amyloid PET-CT image of an AD patient may be corrected using a cerebellum region as a reference region, but the cerebellum region may not be suitable as a reference region for diseases other than *senilis* AD because the deposition of amyloid is observed even in the cerebellum of a patient who has genetic AD and a prion disease.

In some embodiments, the SUVR may indicate a PiB standard uptake value ratio. PiB (Pittsburgh compound B, C-11 Pittsburgh compound) is a beta amyloid tracer, and is a radiopharmaceutical for amyloid PET. A degree of deposited amyloid may be checked based on the taking of a radiopharmaceutical increased due to a combination of PiB and amyloid deposited in the brain.

In some embodiments, the controller 212 may generate a standard brain CT template in an MNI space based on an MNI template calculated from CT images collected from a normal group, and may calculate a whole cortex ROI having a high deposition of beta amyloid by performing CT-guided spatial normalization on PET-CT images of a typical AD patient group and a young control group.

In some embodiments, the controller 212 may specify seven detail regions of cortex based on intersection calculation with AAL atlas within a cortex ROI having a high deposition of beta amyloid in an amyloid PET-CT image.

In some embodiments, the controller 212 may identify the seven detail regions as the results of the intersection calculation with automated anatomical labeling (AAL) atlas (may also be denoted as an "AAL map") within the cortex ROI having a high deposition or taking of beta amyloid based on the amyloid PET-CT image. For example, the seven detail regions may include a frontal cortex, a temporal cortex, a parietal cortex, an occipital cortex, a posterior cingulate cortex, a striatum, and an insula and cingulum cortex.

In some embodiments, to perform the CT-guided spatial normalization may include a normalization correction process. The setting of a control group for measuring the deposition of amyloid and a method thereof will be described in detail with reference to FIG. 3.

Referring to Table 1, the controller 212 may calculate a standardized uptake value ratio (SUVR) and centiloid (CL) for each of the plurality of detail regions, and may derive an equation for directly converting the centiloid or may use an equation for calculating the SUVR and the CL, which is received from the storage unit 214.

TABLE 1

| Tracer | Equations |
| --- | --- |
| FBB | CT-based FBB $dcCL_{Cingulate} = 126.2622 \times SUVR_{FBB\_Cingulate} - 105.6408$ |
|  | CT-based FBB $dcCL_{Frontal} = 183.9885 \times SUVR_{FFB\_Frontal} - 175.7367$ |
|  | CT-based FBB $dcCL_{Occipital} = 166.8818 \times SUVR_{FFB\_Occipital} - 169.5449$ |
|  | CT-based FBB $dcCL_{Parietal} = 165.0618 \times SUVR_{FFB\_Parietal} - 154.5826$ |
|  | CT-based FBB $dcCL_{Temporal} = 159.7466 \times SUVR_{FBB\_Temporal} - 156.9877$ |
|  | CT-based FBB $dcCL_{Striatum} = 136.8557 \times SUVR_{FFB\_Striatum} - 120.1870$ |
|  | CT-based FBB $dcCL_{Insula\_cingulum} = 162.3090 \times SUVR_{FBB\_Insula\_cingulum} - 130.2072$ |
| FMM | CT-based FMM $dcCL_{Cingulate} = 133.1899 \times SUVR_{FFM\_Cingulate} - 117.4537$ |
|  | CT-based FMM $dcCL_{Frontal} = 177.0872 \times SUVR_{FFN\_Frontal} - 162.7210$ |
|  | CT-based FMM $dcCL_{Occipital} = 178.7337 \times SUVR_{FFM\_Occipital} - 174.2443$ |
|  | CT-based FMM $dcCL_{Parietal} = 162.2293 \times SUVR_{FFM\_Parietal} - 148.8902$ |
|  | CT-based FMM $dcCL_{Temppral} = 162.6541 \times SUVR_{FMM\_Temporal} - 155.0908$ |

TABLE 1-continued

| Tracer | Equations |
| --- | --- |
|  | CT-based FMM $dcCL_{Striatum} = 126.3763 \times SUVR_{FMM\_striatum} - 116.5527$ |
|  | CT-based FMM $dcCL_{Insula\_cingulum} = 159.3801 \times SUVR_{FMM\_Insula\_cingulum} - 130.1889$ |

In some embodiments, the controller 212 may finally verify the centiloid calculated using the MRI image.

FIG. 3 is a flowchart for verifying the method and apparatus for diagnosing AD using a PET-CT image according to an embodiment of the present disclosure.

Referring to FIG. 3, in order to calculate a centiloid based on a PET-CT image, the apparatus for diagnosing AD using a PET-CT image may first group experiment participants and secure PET-CT images using a PET-CT apparatus (S310).

In this case, the experiment participants may be composed of patients, including a young control (YC), an old control (OC), a mild cognitive impairment (MCI), subcortical vascular dementia, and Alzheimer's disease dementia (ADD). The experiment participants may take tests using an amyloid PET apparatus to which two radio-pharmaceutical tracers (FBB and FMM) have been applied and tests using a T1-weighted magnetic resonance imaging (MRI) apparatus. In order to define a whole cortex volume of interest (VOI) in which amyloid has been deposited based on each of the two radio-pharmaceutical tracers, the experiment participants may include an ADD patient whose amyloid PET is positive with respect to the two radio-pharmaceutical tracers and an OC patient whose amyloid PET is negative with respect to the two radio-pharmaceutical tracers.

Thereafter, the apparatus for diagnosing AD using a PET-CT image may generate a centiloid using the secured PET-CT image.

In some embodiments, the apparatus for diagnosing AD using a PET-CT image may register an individual MRI image with an MNI template (MNI-152 template) based on an SPM-based standard centiloid process, and then may register an individual PET-CT image with the corresponding MRI image. In some embodiments, thereafter, the apparatus may spatially normalize a T1-weighted MRI based on a conversion parameter using an SPM8 integration and dividing method.

In some embodiments, the apparatus for diagnosing AD using a PET-CT image may use a standard centiloid global cortical target volume of interest (CTX VOI) and a whole cerebellum (WC) mask. The WC may be used as a reference region in a quantitative analysis of FBB and FMM PET images.

In some embodiments, the apparatus for diagnosing AD using a PET-CT image may generate an MR-based FBB-FMM global CTX VOI (S320) in the AD patients (AD-CTX) and the old control (OC-CTX) using an SUVR parametric image of spatially normalized FBB and FMM PET images.

In some embodiments, the apparatus for diagnosing AD using a PET-CT image may generate a mask based on a difference value between the AD-CTX and the OC-CTX in order to generate the FBB-FMM global CTX VOI. As a result, two masks for the FBB and FMM PETs may be generated.

In some embodiments, the apparatus for diagnosing AD using a PET-CT image may generate the FBB-FMM global CTX VOI, including an AD-related common brain amyloid deposition region for FBB and FMM PET tracers, by crossing the two masks and determining a threshold value of the crossed masks. In some embodiments, the apparatus for diagnosing AD using a PET-CT image may calculate an individual dcSUVR value and a SUVR standard value using the MR-based FBB-FMM CTX VOI and a standard CTX VOI, respectively.

using the CT image without using an MRI image in an embodiment of the present disclosure.

In some embodiments, referring to Table 2, the apparatus for diagnosing AD using a PET-CT image may use the previously calculated FBB-FMM global CTX VOI in order to calculate a centiloid.

TABLE 2

| | CT-based FBB-FMM CTX VOI | | | | MR-based FBB-FMM CTX VOI | | | |
|---|---|---|---|---|---|---|---|---|
| | FBB | | FMM | | FBB | | FMM | |
| | dcSUVR | dcCL | dcSUVR | dcCL | dcSUVR | dcCL | dcSUVR | dcCL |
| ADD | 1.52 ± 0.30 | 100 ± 50.68 | 1.51 ± 0.27 | 100 ± 46 | 1.56 ± 0.28 | 100 ± 46.71 | 1.54 ± 0.26 | 100 ± 42.78 |
| YC | 0.94 ± 0.05 | 0.00 ± 8.08 | 0.92 ± 0.05 | 0.00 ± 7.71 | 0.95 ± 0.03 | 0.00 ± 5.03 | 0.93 ± 0.03 | 0.00 ± 5.05 |

In some embodiments, the apparatus for diagnosing AD using a PET-CT image may configure a brain CT template, may generate the PET image and the CT image as a single image (i.e., co-registration), and then may generate a standard brain CT template for CT-guided spatial normalization. The apparatus for diagnosing AD using a PET-CT image may generate a brain PET-CT template from the PET-CT image based on a Hounsfield unit (HU) correction for a brain tissue.

In some embodiments, the brain CT template may be generated by changing the direction of the PET-CT image, adjusting contrast, or applying Gaussian smoothing (e.g., Gaussian smoothing 8 mm)).

In some embodiments, the apparatus for diagnosing AD using a PET-CT image may spatially normalize an individual T1 MR image in the MNI space, and may apply a spatial normalization parameter of the T1 MR image to a corresponding HU-corrected CT image. The HU-corrected CT image may be turned over to generate a symmetrical template.

In some embodiments, the apparatus for diagnosing AD using a PET-CT image may generate a CT-based FBB-FMM global CTX VOI (S330). The apparatus for diagnosing AD using a PET-CT image may perform HU correction processing on each CT image. A PET image of each of FBB and FMM may be registered along with a corresponding HU-corrected CT image. Such a PET image may be spatially normalized using a normalization parameter for each HU-corrected CT image in the MNI space based on the generated brain CT template. In some embodiments, the apparatus for diagnosing AD using a PET-CT image may generate a global CTX VOI ("FBB-FMM global CTX VOI"), which may be used in FBB-FMM in common, in the same manner as in the MR-based FBB-FMM method using the normalized PET image of each of FBB and FMM. Furthermore, the apparatus for diagnosing AD using a PET-CT image may generate individual dcSUVR and an SUVR standard based on the CT-based global FBB-FMM CTX VOI and the standard CTX VOI. The SUVR standard may mean an SUVR calculated based on a CTX VOI generated as PiB in Klunk's thesis (2015, The Centiloid Project), and may be CTX different from CTX calculated based on dcCL. A method of 2020 July; 47 (8):1938-1948. doi: 10.1007/s00259-019-04596-x. Epub 2019 Dec. 13, posted on Eur J Nucl Med Mol Imaging, may be applied to the FBB-FMM global CTX VOI. In this case, PET images of ADCI and OC were used in this procedure, but is different in that it has typical ADD,OC and calculates the FBB-FMM global CTX VOI dcSUVR may be obtained by applying the CT-based FBB-FMM global CTX VOI to the FBB and FMM PETs, and the validity of a CT-based centiloid may be verified using the MR-based method.

$$CL = 100 \times (SUVR_{ind} - SUVR_{YC-0})/(SUVR_{ADD-100} - SUVR_{YC-0}) \quad (1)$$

Equation 1 may be used to calculate the centiloid (direct comparison of FBB-FMM CL, dcCL). In this case, the $SUVR_{ind}$ indicates an individual SUVR value of each of all YC-0 and ADD-100 participants, and the $SUVR_{YC-0}$ and the $SUVR_{ADD-100}$ indicate average SUVR values of the respective groups.

In some embodiments, the apparatus for diagnosing AD using a PET-CT image may calculate the centiloid of a detail region based on a difference value between previously generated FBB-FMM global CTX VOIs (S340). The detail region VOI may be defined to be intersected between generated FBB-FMM global CTX VOIs, showing high amyloid deposition in all of the FBB and FMM PETs and the AAL map. All of lower regions that intersect the FBB-FMM global CTX VOI may be used, and may include the seven detail regions, such as a frontal cortex, a temporal cortex, a parietal cortex, an occipital cortex, a posterior cingulate cortex, a striatum, and an insula and cingulum cortex.

A detail region dcSUVR value and detail region dcCL value of a corresponding region for the CT-based and MR-based methods may be calculated using a dcCL conversion equation for the seven detail regions. A conversion equation for calculating the centiloids of the seven detail regions may be derived from dcSUVR and dcCL of the detail region.

In some embodiments, the apparatus for diagnosing AD using a PET-CT image may verify the CT-based method using a centiloid calculation method based on an MR detail region.

Figure 4:
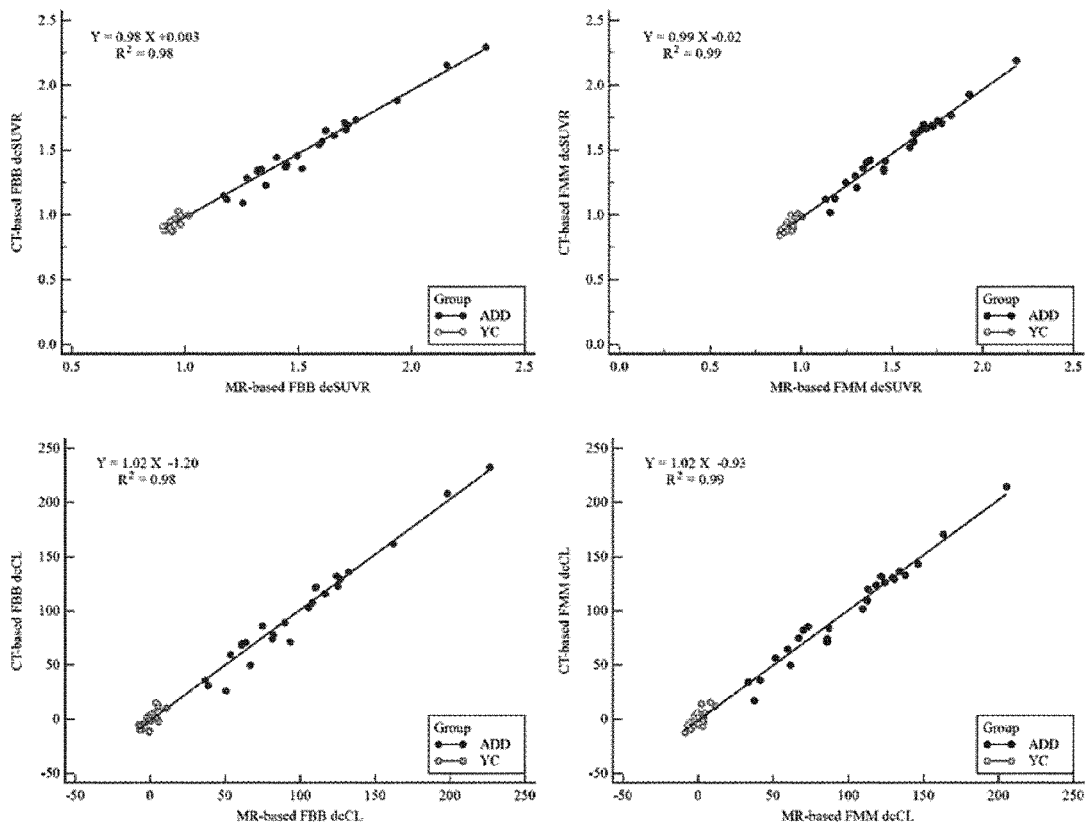
FIG. 4 is a diagram for describing correlations between dcSUVRs and dcCL based on a global CTX volume of interest (VOI) using an MR-based method and a global CTX VOI using a CT-based method according to an embodiment of the present disclosure.

A linear regression for the correlation may be performed between the CT-based method and the MR-based method for the FBB and FMM PETs. From FIG. 4, it may be seen that for the reliability of the FBB-FMM global CTX VOI generated by the CT-based method, dcSUVRs and dcCL based on the global CTX VOI using the MR-based method and the global CTX VOI using the CT-based method have a correlation.

Figure 5:
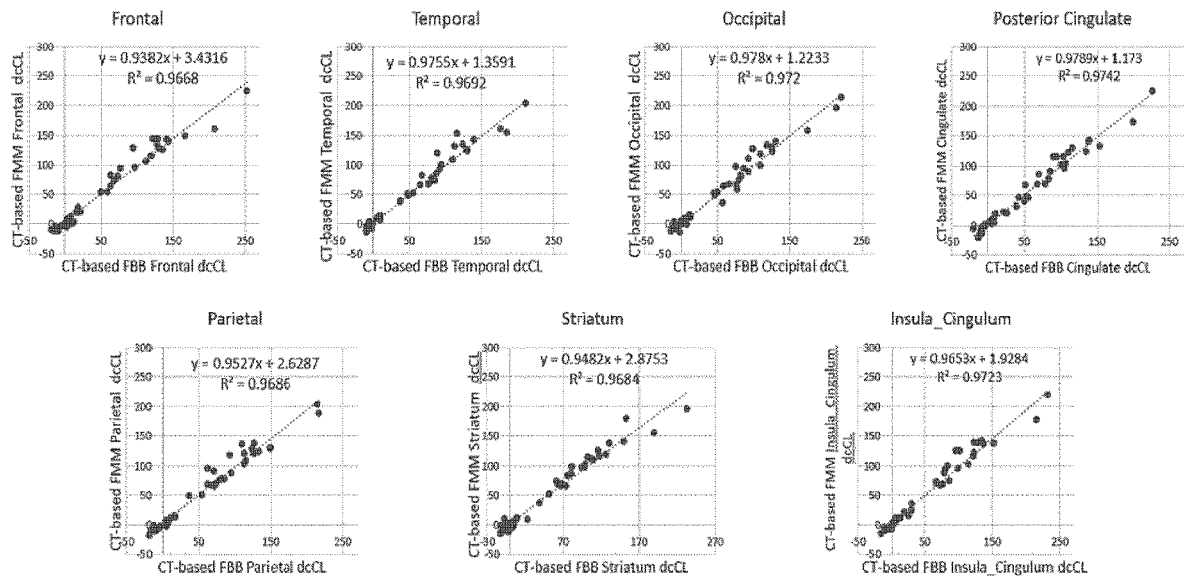
FIG. 5 is a diagram for describing that correlations between centiloids for seven detail regions are analyzed between the CT-based method and the MR-based method according to an embodiment of the present disclosure.

Referring to FIG. 5, it may be interpreted that correlations between the centiloids of the seven detail regions are analyzed between the CT-based method and the MR-based method because a primary object is to demonstrate the method of calculating the centiloid of the CT-based detail region by expanding up to the centiloid of the detail region in the entire volume.

Figure 6:
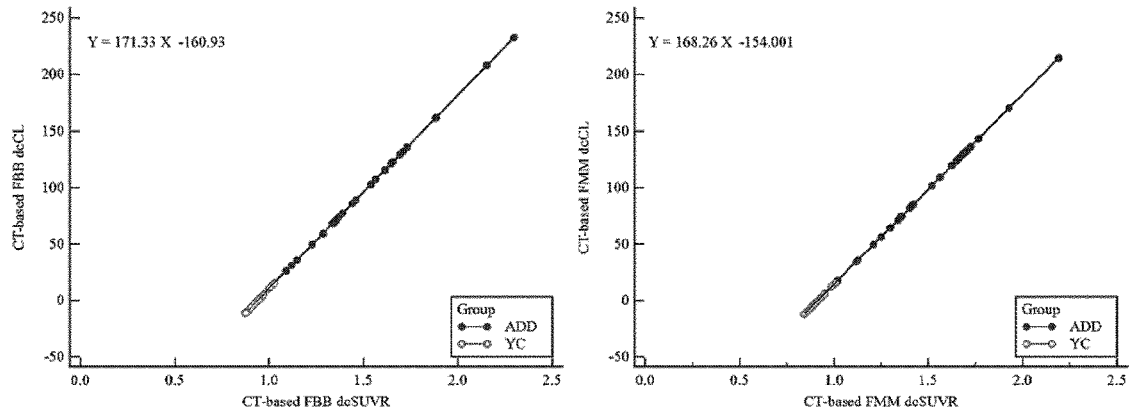
FIG. 6 is a diagram for describing linear correlations between centiloids obtained based on a standard global cortex target VOI and dcCL obtained using the CT-based method according to an embodiment of the present disclosure.

FIG. 6 illustrates a linear equation (Y=171.33 X−160.93) between dcSUVR and dcCL for FBB using the CT image and a linear equation (Y=168.26 X−154.001) between dcSUVR and dcCL for FMM using the CT image.

dcCL may be calculated from dcSUVR based on the linear equation between dcSUVR and dcCL of each of FBB and FMM using the CT images.

Figure 7:
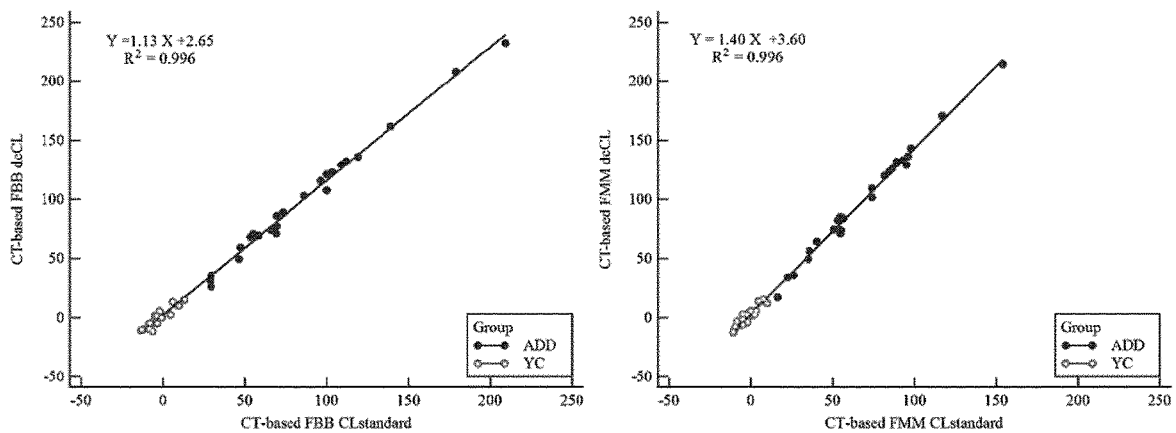
FIG. 7 is a diagram for describing linear correlations between centiloids obtained based on a standard global cortex target VOI and dcCL obtained using the MR-based method according to an embodiment of the present disclosure.

FIG. 7 shows a result of a comparison (X axis: the standard centiloid method, Y axis: the dcCL method) between centiloid scores according to the standard centiloid methods and centiloid scores according to the dcCL method for FBB and FMM. In the standard centiloid methods, a comparison based on only the global CTX VOI may be performed because there is no divided detail region.

Figure 8:
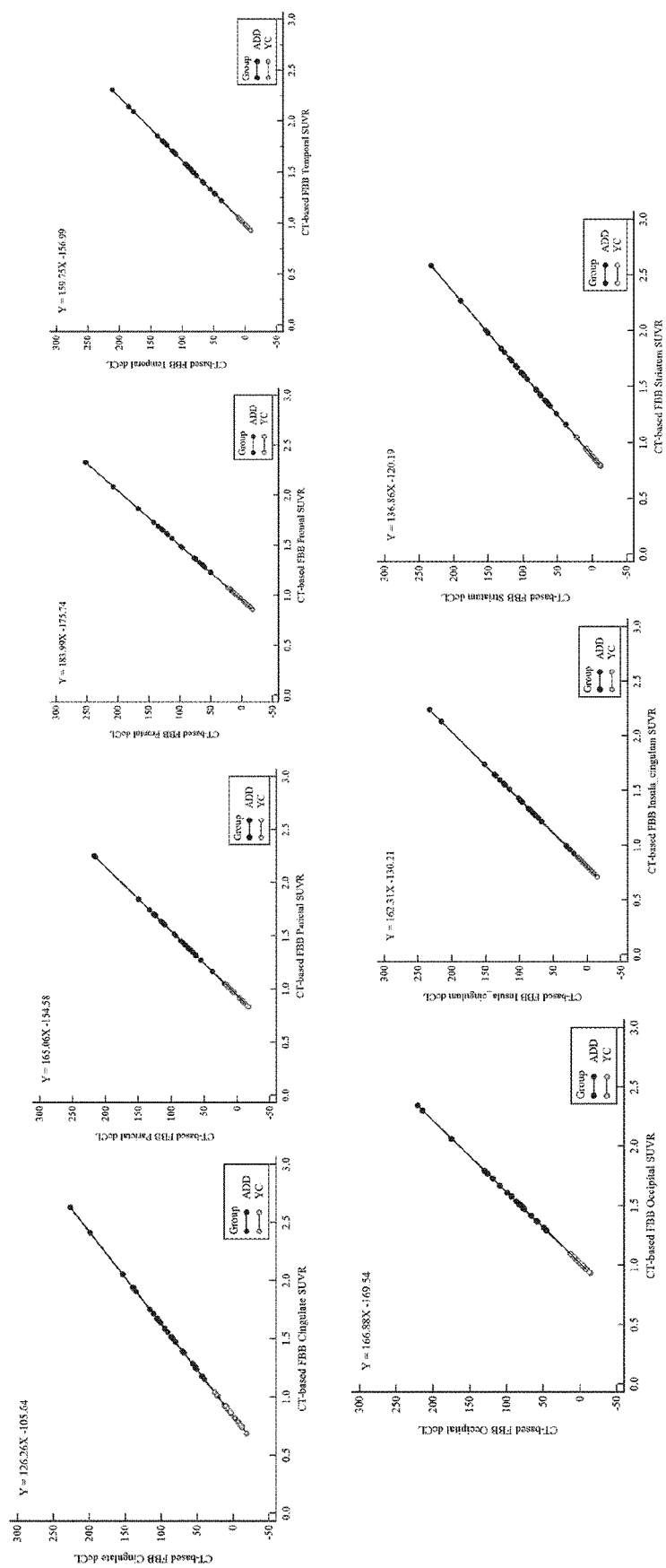
FIG. 8 is a diagram for describing linear relations between SUVRs and centiloids to which FBB has been applied with respect to seven detail regions according to an embodiment of the present disclosure.
Figure 9:
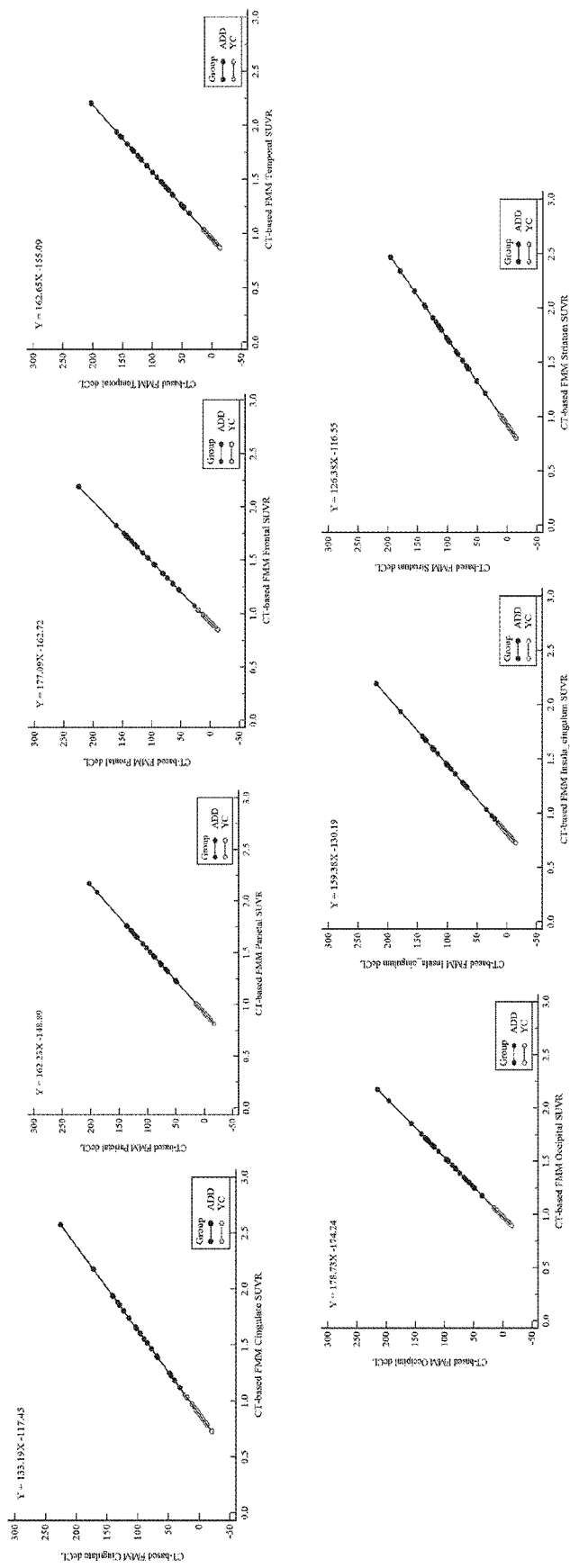
FIG. 9 is a diagram for describing linear relations between SUVRs and centiloids to which FMM has been applied with respect to seven detail regions according to an embodiment of the present disclosure.

FIG. 8 shows linear regression between the SUVRs to which FBB for the seven detail regions has been applied and the centiloids. FIG. 9 shows linear regression between the SUVRs to which FMM for the seven detail regions has been applied and the centiloids. If dcSUVR calculated using a centiloid VOI mask for each detail region is present, a centiloid score for each detail region may be calculated through a linear equation for each detail region using the dcSUVR as an input.

The method and apparatus for diagnosing AD using a PET-CT image according to an embodiment of the present disclosure can diagnose AD, which is caused by beta amyloid, with respect to a patient on which an MRI scan cannot be performed.

Furthermore, the method and apparatus for diagnosing AD using a PET-CT image according to an embodiment of the present disclosure can reduce expenses and time consumed for a diagnosis of AD because MRI scan results are not used.

Furthermore, the method and apparatus for diagnosing AD using a PET-CT image according to an embodiment of the present disclosure has high accuracy for a diagnosis of AD because they are based on a centiloid for each detail region of the brain and a different degree of amyloid deposited in a brain portion for each patient can be considered.

According to the embodiments of the present disclosure, there may be provided a computer-readable recording medium in which a program for executing the aforementioned method in a computer has been recorded. In other words, the aforementioned method may be written in the form of a computer-executable program, and may be implemented in a general-purpose digital computer that drives the program using a computer-readable medium. Furthermore, the structure of data used in the aforementioned method may be recorded in a computer-readable medium through several means. A recording medium in which an executable computer program or code for performing various methods of the present disclosure is recorded should not be understood to include transitory targets, such as carrier waves or signals. The computer-readable medium may include storage media, such as magnetic storage media (e.g., a ROM, a floppy disk and a hard disk) and optical reading media (e.g., a CD-ROM and a DVD).

Although the present disclosure have been described in detail above through the representative embodiments, a person having ordinary skill in the art to which the present disclosure pertains will understand that the embodiments may be modified in various ways without departing from the category of the present disclosure. Accordingly, the scope of rights of the present disclosure should not be limited to the aforementioned embodiments, but should be defined by all changed or modified forms derived from the appended claims and equivalent concepts thereof.

What is claimed is:

1. A method of diagnosing Alzheimer's disease using a positron emission tomography-computed tomography (PET-CT) image, the method comprising:
    generating a standard brain CT template in a Montreal Neurological Institute (MNI) region based on a CT image calculated from a PET-CT apparatus;
    calculating a whole cortex volume of interest (VOI) for a plurality of detail regions configured to be used in $^{18}$F-florbetaben (FBB) and $^{18}$F-flutemetamol (FMM) in common within a cortex ROI region in which a deposition of beta amyloid protein is equal to or higher than a given value based on the standard brain CT template; and
    calculating a centiloid of each of the plurality of detail regions based on a VOI and amyloid standardized uptake value ratio (SUVR) of each of the plurality of detail regions.

2. The method of claim 1, wherein the plurality of detail regions comprises at least two of a frontal cortex, a temporal cortex, a parietal cortex, an occipital cortex, a posterior cingulate cortex, a striatum, and an insula and cingulum cortex.

3. The method of claim 1, wherein the centiloid is calculated as a value obtained by subtracting a second previously calculated value from a result value of a real number times a first previously calculated value with respect to the amyloid SUVR.

4. The method of claim 1, wherein the PET-CT image comprises a PET image and a CT image as a result of a beta amyloid PET apparatus.

5. An apparatus for diagnosing Alzheimer's disease using a PET-CT image, comprising:
    a communication unit configured to receive a CT image from a PET-CT apparatus; and
    a controller operatively associated with the communication unit,
    wherein the controller is configured to generate a standard brain CT template in a Montreal Neurological Institute (MNI) region based on the CT image calculated from the PET-CT apparatus;
    wherein the controller is configured to calculate a whole cortex volume of interest (VOI) for a plurality of detail regions configured to be used in $^{18}$F-florbetaben (FBB) and $^{18}$F-flutemetamol (FMM) in common within a cortex ROI region in which a deposition of beta amyloid protein is equal to or higher than a given value based on the standard brain CT template; and
    wherein the controller is configured to calculate a centiloid of each of the plurality of detail regions based on a VOI and amyloid standardized uptake value ratio (SUVR) of each of the plurality of detail regions.

6. The apparatus of claim 5, wherein the plurality of detail regions comprises at least two of a frontal cortex, a temporal cortex, a parietal cortex, an occipital cortex, a posterior cingulate cortex, a striatum, and an insula and cingulum cortex.

7. The apparatus of claim 5, wherein the centiloid is calculated as a value obtained by subtracting a second previously calculated value from a result value of a real number times a first previously calculated value with respect to the amyloid SUVR.

8. The apparatus of claim 5, wherein the PET-CT image comprises a PET image and a CT image as a result of a beta amyloid PET apparatus.

\* \* \* \* \*